United States Patent [19]

Suga

[11] Patent Number: 4,544,995

[45] Date of Patent: Oct. 1, 1985

[54] APPARATUS FOR TESTING LIGHT FASTNESS OF A MATERIAL

[76] Inventor: Shigeru Suga, 20-2 Yoyogi, 5-chome, Shibuya-ku, Tokyo, Japan

[21] Appl. No.: 501,397

[22] Filed: Jun. 6, 1983

[51] Int. Cl.[4] .......................... G01N 17/00; F21S 3/00
[52] U.S. Cl. ..................................... 362/225; 362/230; 362/234; 362/362; 73/432 SD
[58] Field of Search .................... 362/1, 2, 33, 97, 125, 362/234, 230, 231, 217, 225, 362, 147; 73/150, 159, 432 SD; 313/17

[56] References Cited

U.S. PATENT DOCUMENTS

| | | | |
|---|---|---|---|
| 3,271,570 | 9/1966 | Kruger | 362/225 |
| 3,488,681 | 1/1970 | Mita et al. | 73/159 |
| 3,500,682 | 3/1970 | Newfield | 73/150 |
| 3,576,125 | 4/1971 | Kockett | 73/150 |
| 3,886,791 | 6/1975 | Grossman | 73/150 R |
| 3,889,531 | 6/1975 | Suga | 73/150 R |
| 3,983,742 | 10/1976 | Suga | 73/150 |
| 3,988,609 | 3/1976 | Lewin | 362/217 |
| 4,012,954 | 3/1977 | Klippert | 73/150 R |
| 4,383,289 | 5/1983 | Lewin | 362/217 |
| 4,391,522 | 7/1983 | Schmid et al. | 73/150 |

OTHER PUBLICATIONS

ASTM53-77, Standard Recommended Practice for Operating Light-and Water-Exposure Apparatus, (Flourescent UV-Condensation Type) for Exposure or Nonmetallic Materials, pp. 1071-1076, (1977).

Primary Examiner—Andrew M. Dolinar
Attorney, Agent, or Firm—Wenderoth, Lind & Ponack

[57] ABSTRACT

An apparatus for testing light fastness of a material having a housing with a test chamber therein and two downwardly and outwardly inclined specimen supporting walls on opposite sides of the chamber and two rows of horizontally positioned equal intensity ultraviolet fluorescent lamps one lying generally along each of the specimen supporting walls, with four lamps in each row. The uppermost lamp in each row is spaced downwardly from the upper edge of the specimen supporting wall and the next lower lamp is spaced above the midpoint of the vertical dimension of the wall substantially equal distances, the uppermost and next lower lamps being spaced from each other slightly less than twice the equal distance. The still next lower lamp is spaced downwardly from the midpoint and the lowermost lamp is spaced upwardly from the lower edge of the specimen supporting wall slightly more than half the distance the still next lower lamp is spaced downwardly from the midpoint, the lowermost lamp being spaced from the still next lower lamp slightly less than the still next lower lamp is spaced from the midpoint. The uppermost lamp is spaced perpendicular to the specimen supporting wall about one-sixth of the vertical dimension thereof, the lowermost lamp is spaced slightly closer to the wall than the uppermost lamp, the still next lower lamp is spaced slightly farther from the wall than the uppermost lamp, and the next lower lamp is spaced still slightly farther from the wall than the still next lower lamp.

3 Claims, 6 Drawing Figures

APPARATUS FOR TESTING LIGHT FASTNESS OF A MATERIAL

This invention relates to a testing apparatus for testing a material for light fastness and deterioration under light, and more particularly to such a testing machine using ultraviolet fluorescent lamps as light sources.

BACKGROUND OF THE INVENTION AND PRIOR ART

A conventional testing apparatus using ultraviolet fluorescent lamps as shown in FIG. 1 has eight equal intensity ultraviolet fluorescent lamps 1 provided in a test chamber 2 and arranged in two symmetric downwardly divergent rows when viewed in cross-section. Specimens 3 to be tested are attached to two opposite specimen supporting walls of the housing of the test apparatus so as to face inwardly toward the fluorescent lamps and receive the light radiated therefrom. In the machine shown, there are two specimens, an upper and a lower one. However, there may be only a single specimen or more than two. The rear surfaces of the specimen 3 are exposed to the atmospheric air outside the machine. Outside air is drawn through a blower 5 and heated by a heater 6 and the thus heated air is blown into the interior of the chamber 2 through a hot air discharge port 4 to regulate the temperature in the chamber 2. Water in moisture supply tanks 7 is made hot by heaters 8 therein and evaporated to thereby supply moisture into the chamber 2.

An example of the use of this testing machine will now be described. In the above-described testing machine, the ultraviolet rays are applied to the specimens 3 at a temperature of 60° C. for 16 hours, and the fluorescent lamps 1 are then turned off and the interior of the chamber 2 is kept at 50° C. for 8 hours. These two steps, which constitute one cycle of a deterioration testing operation, are repeated continuously. While the fluorescent lamps are off, the humidity in the chamber 2 is high, and the rear surfaces of the specimens are exposed to the outside air at a low temperature. Accordingly, the surfaces of the specimens are wetted due to condensation. Thus, the wetting of the specimens, the applying of ultraviolet rays thereto, and the drying thereof are repeated, which speeds the deterioration of the specimens.

However, this testing machine has a large drawback in that the reproducibility of test results is low. When the same deterioration test of 3000 hours is carried out with a plurality of these testing machines, they require anywhere from 2000 to 4000 hours to obtain the same test results. Thus, the reproducibility of results using this type of testing machine is extremely low due to such a large error.

OBJECTS AND BRIEF SUMMARY OF THE INVENTION

It is an object of the invention to provide a testing machine of the above described type which overcomes this drawback.

It is a further object of the invention to provide a testing machine which produces more accurately reproducible results.

To achieve these objects the present invention provides a light fastness testing apparatus having a housing with a test chamber therein and two downwardly and outwardly inclined specimen supporting walls on opposite sides of the chamber and two rows of horizontally positioned equal intensity ultraviolet fluorescent lamps, one lying generally along each of the specimen supporting walls, with four lamps in each row. The uppermost lamp in each row is spaced downwardly from the upper edge of the specimen supporting wall and the next lower lamp is spaced above the midpoint of the vertical dimension of the specimen supporting wall substantially equal distances. The uppermost and next lower lamps being spaced from each other slightly less than twice the equal distance. The still next lower lamp is spaced downwardly from the midpoint and the lowermost lamp is spaced upwardly from the lower edge of the specimen supporting wall slightly more than half the distance the still next lower lamp is spaced downwardly from the midpoint, the lowermost lamp being spaced from the still next lower lamp slightly less than the still next lower lamp is spaced from the midpoint. The uppermost lamp is spaced perpendicular to the specimen supporting wall about one-sixth of the vertical dimension of the specimen supporting wall, the lowermost lamp is spaced slightly closer to the specimen supporting wall than the uppermost lamp, the still next lower lamp is spaced slightly farther from the specimen supporting wall than the uppermost lamp, and the next lower lamp is spaced still slightly farther from the specimen supporting wall than the still next lower lamp.

BRIEF DESCRIPTION OF THE DRAWINGS

The invention will now be described in greater detail in connection with the accompanying drawings in which.

DETAILED DESCRIPTION OF THE INVENTION

Figure 1:
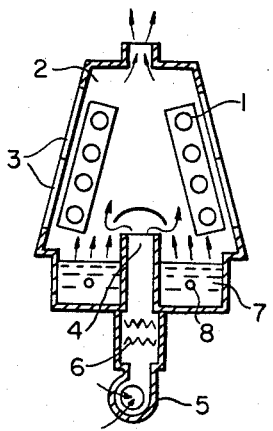
FIG. 1 is a schematic sectional end view of a conventional testing machine using ultraviolet fluorescent lamps.
Figure 2:
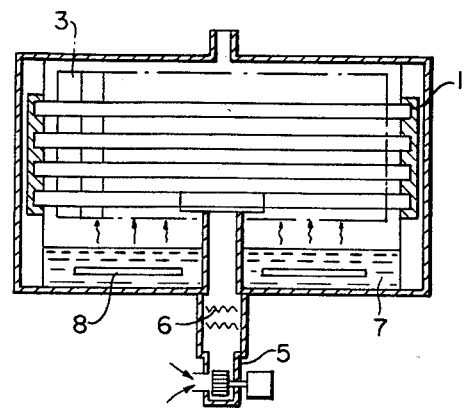
FIG. 2 is a schematic side elevation view, partly in section, of the machine of FIG. 1.
Figure 3:
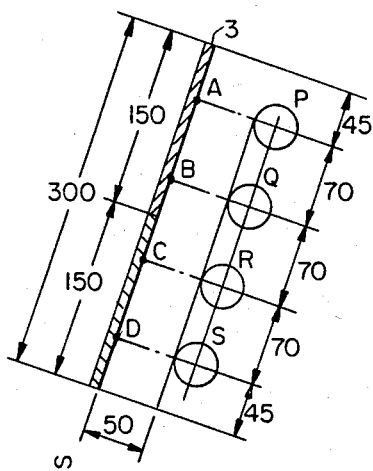
FIG. 3 is a diagram showing the relative positions of the fluorescent lamps in the machine of FIGS. 1 and 2.
Figure 4:
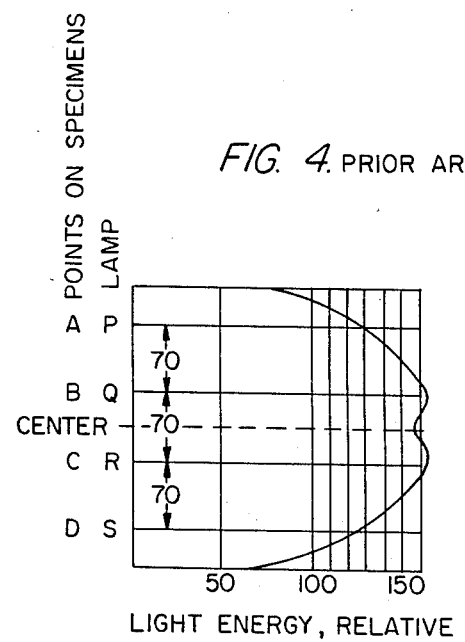
FIG. 4 is a diagram showing calculated values representing the distribution of light energy on the surface of a specimen or specimens.

FIG. 3 shows the relative sizes and positions of lamps and the specimens in the above-described conventional testing machine. These sizes are according to ASTM G53. As can be understood from this drawing, the intensity of light energy on the surface of the specimens is the highest on the portion thereof which is between points B and C opposed to the lamps Q and R, and suddenly decreases on the portions of the surface of the specimens which are above the point A opposed to the lamp P and below the point D opposed to the lamp S, as a distance from the points A and D increases on these portions of the surfaces of the specimen. The calculated values of light energy on various points on the surfaces of the specimens are shown in FIG. 4. The actual values of light energy do not agree with the calculated values due to the influence of the light from the fluorescent lamps on the opposite side of the chamber 2, and the irregular reflection of light occurring in the chamber. The actual measured intensity of light energy at the above-mentioned points is shown in Table 1. According to Table 1, the intensity of light energy on the points B and C on the surfaces of the specimens shown in FIG. 3 is substantially equal and is the highest intensity, and the intensity of light energy on the points A and D is lower than that on the points B and C. Moreover, the distance between the point D and a lamp on the opposite side of the chamber therefrom is large as compared with that between the point A and a lamp on the opposite side of the chamber therefrom. Accordingly, the intensity of light energy on the point D is the lowest, being 65% of that on the point B.

TABLE 1

| Points on the specimen | A | B | C | D |
| --- | --- | --- | --- | --- |
| Light energy (mW/cm$^2$) | 1.58 | 2.05 | 1.97 | 1.34 |
| Ratio (based on the intensity of light energy on the point B, which is expressed as 100) | 77.1 | 100 | 96.1 | 65.5 |

Note:
Distance between adjacent lamps: 70 mm
Distance between adjacent measuring points: 70 mm Since the light energy is distributed in such a manner, the degrees of deterioration, which are measured during a test, of the upper and lower specimens, or if there is only one specimen, the upper and lower portions thereof, naturally differ. Also, different portions of the same specimen, where there is more than one, undergo different degrees of deterioration. Therefore, there are no basic points on the specimens at which a rating of the deterioration can be said to be the correct rating for the entire specimen, so that the deterioration of the specimens cannot be rated accurately. In addition, no reproducible deterioration tests can be conducted.

Figure 5:
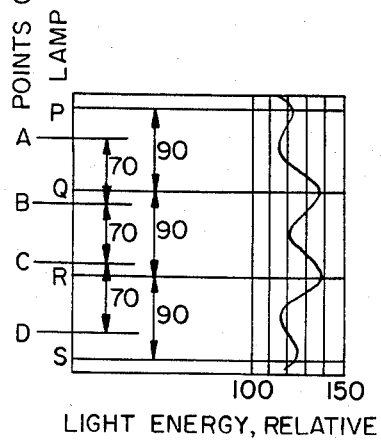
FIG. 5 is a diagram showing calculated values representing the distribution of light energy on the surface of a specimen or specimens where the distances between lamps are increased.
Figure 6:
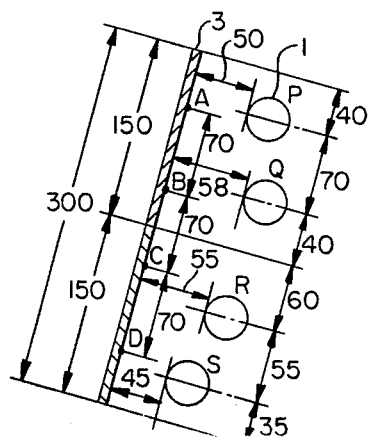
FIG. 6 is a diagram showing the relative positions of lamps in a tester according to the present invention.

To overcome these drawbacks encountered in the conventional deterioration tester, in the present invention the positions of the lamps have been adjusted to make the light energy falling on the specimens more uniform over the entire area of the specimens. For example, the distance between the midpoints of adjacent lamps, i.e. the midpoints of the cross-sections of the lamps as shown in FIGS. 3 and 6, which is 70 mm in the conventional tester, is increased to 90 mm and the distance between the specimen or specimens and lamps opposed thereto left the same as in the conventional tester, i.e. at 50 mm, the calculated values of the distribution of light energy on various points on the specimen or specimens are as shown in FIG. 5. As is clear from the drawing, the more the distance between adjacent lamps is increased beyond 70 mm, the distance at which the adjacent lamps in the conventional tester are spaced the more the distribution of light energy on the surface of the specimens can be improved. Accordingly, when the distance between lamps and the distance between the surface of the specimen or specimens and the lamps are both suitably adjusted, the distribution of light energy on the surfaces of the specimens can be made more uniform. According to the data shown in Table 1, the intensity of light energy is a little low at the point A, and extremely low at the point D. In order to increase the intensity of light energy on these two points, the lamps P and S are moved closer to the surface of the specimens, and the distance between the respective lamps and the adjacent lamps is also changed. Such distance changes bring about good results.

According to the present invention, the surfaces of the intermediate lamps Q and R closest to the specimen or specimens are disposed at positions farther away from the surface of the specimen or specimens, and the distance between the lamps Q and R is increased as compared with the conventional tester. Also, the distance between the similar surfaces of lamps P and S and the surface of the specimen or specimens is made equal to or less than that in the conventional tester, and the distances between the lamps P and S and the center line of the specimen supporting side wall of the housing (the lower edge of an upper specimen and the upper edge of a lower specimen) are increased upward and downward, respectively.

That is, the uppermost lamp P in each row is spaced downwardly from the upper edge of the specimen supporting wall (all spacings are parallel to the wall surface) and the next lower lamp Q is spaced above the midpoint of the dimension of the specimen supporting wall from the top edge to the bottom edge thereof substantially equal distances, the lamps P and Q being spaced from each other slightly less than twice said equal distance. The still next lower lamp R i.e. the third lowest lamp, is spaced downwardly from said midpoint and the lowermost lamp S is spaced upwardly from the lower edge of the specimen supporting wall slightly more than half the distance said still next lower lamp R is spaced downwardly from said midpoint, said lamps R and S being spaced slightly less than said lamp R is spaced from midpoint.

The surface of the uppermost lamp P closest to the wall is spaced perpendicular to the specimen supporting wall 3 about one-sixth of the vertical dimension of the specimen supporting wall, the lowermost lamp S is spaced slightly closer to the specimen supporting wall than the uppermost lamp P, the still next lower lamp R is spaced slightly farther from the specimen supporting wall than the uppermost lamp P, and the next lower lamp Q is spaced still slightly farther from the specimen supporting wall than the still next lower lamp R.

An embodiment of the present invention is shown in FIG. 6. In this embodiment, the distance between lamp P and the surface of the specimen is 50 mm, which is equal to the corresponding distance in the conventional tester, the distance between the lamp Q and the surface of the specimen is 58 mm, and the distance along the surface of the sample between the lamps Q and P is 70 mm, which is equal to the corresponding distance in the ASTM G53 conventional tester. The lamps were FS40 ultraviolet fluorescent lamps, 1220 mm long. The distance between the lamp R and the surface of the specimen is 55 mm, and the distance between the lamps R and Q is 100 mm, the distance between the centerline of the specimen and the lamp Q being 40 mm, and a distance between the centerline and the lamp R being 60 mm. The distance between the lamp S and the surface of the specimens is 45 mm, and the distance along the surface of the specimens between the lamps S and R is 55 mm. The distribution of light energy on the surface of the specimens irradiated with the lamps in such positional relationships is shown in Table 2. As is clear from this table, the distribution of light energy on the surface of the specimens is quite uniform.

The foregoing example is for specific positional relationships between the specimens and the lamps. Suitable ranges of these positional relationships of the specimens and the lamps are shown in Table 3.

TABLE 2

| Points on the specimen | A | A-B | B | B-C | C | C-D | D |
|---|---|---|---|---|---|---|---|
| Light energy (mW/cm$^2$) | 2.48 | 2.58 | 2.80 | — | 2.91 | 2.91 | 2.48 |
| Ratio (based on the intensity of light energy on the point B which is expressed as 100) | 88.6 | 92.1 | 100 | — | 103.9 | 103.9 | 88.6 |

Note:
Distance between the measuring points: 70 mm
The intensity of light energy on the point B is regulated to 2.80 mW/cm$^2$.

TABLE 3

| Lamp | Distance (mm between the surface of a specimen and those of lamps) | Distance (mm) (along the surface of a specimen) between the horizontal center line on a specimen and lamps |
|---|---|---|
| P | 45–50 | 106–135 |
| Q | 51–60 | 36–60 |
| R | 51–60 | 36–60 |
| S | 45–50 | 106–135 |

What is claimed is:

1. In a light fastness testing apparatus having a housing with a test chamber therein and two downwardly and outwardly inclined specimen supporting walls on opposite sides of said chamber and two downwardly and outwardly extending rows of horizontally positioned equal intensity ultraviolet fluorescent lamps one lying generally along each of the specimen supporting walls, with four lamps in each row, the improvement comprising:

the uppermost lamp in each row having the midpoint thereof spaced downwardly from the upper edge of the specimen supporting wall a distance substantially equal to the distance that the midpoint of the next lower lamp is spaced above the midpoint of the dimension of the specimen supporting wall which wall dimension is measured along the wall from the top to the bottom thereof, the midpoints of the uppermost and next lower lamps being spaced from each other slightly less than twice said equal distance in a direction parallel to said specimen supporting wall, the midpoint of the third lowest lamp being spaced downwardly from said wall midpoint and the midpoint of the lowermost lamp being spaced upwardly from the lower edge of the specimen supporting wall slightly more than half the distance said third lowest lamp is spaced downwardly from said wall midpoint and in a direction parallel to said specimen supporting wall, said lowermost lamp being spaced from said third lowest lamp slightly less than said third lowest lamp is spaced from said wall midpoint; the surface of the uppermost lamp closest to said specimen supporting wall being spaced perpendicular to the specimen supporting wall about one-sixth of the dismension of the specimen supporting wall along the wall from the top to the bottom thereof, the surface of the lowermost lamp being spaced slightly closer to the specimen supporting wall than the uppermost lamp, the surface of the third lowest lamp being spaced slightly farther from the specimen supporting wall than the uppermost lamp, and the surface of the next lower lamp being spaced still slightly farther from the specimen supporting wall than the thrid lowest lamp.

2. The improvement as claimed in claim 1 in which the uppermost lamp in each row is spaced 40 mm along the wall from the upper edge of the specimen supporting wall and the next lower lamp is spaced along the wall 40 mm above the midpoint of the specimen supporting wall, and said uppermost and next lower lamps being spaced 70 mm, the third lowest lamp is spaced 60 mm along the wall from said wall midpoint and the lowermost lamp is spaced 35 mm along the wall from the lower edge of the specimen supporting wall and said lowermost and third lowest lamps being spaced 55 mm, the uppermost lamp being spaced 50 mm perpendicular to the specimen supporting wall, the lowermost lamp being spaced 45 mm from the specimen supporting wall, the third lowest lamp being spaced 55 mm from the specimen supporting wall, and the next lower lamp being spaced 58 mm from the speciment supporting wall.

3. In a light fastness testing apparatus having a housing with a test chamber therein and two downwardly and outwardly inclined specimen supporting walls on opposite sides of said chamber and two downwardly and outwardly extending rows of horizontally positioned equal intensity ultraviolet fluorescent lamps one lying generally along each of the specimen supporting walls, with four lamps in each row, the improvement comprising:

the midpoint of the uppermost lamp in each row being spaced along the wall above the midpoint of the dimension of the specimen supporting wall which wall dimension is measured along the wall from the top edge to the bottom edge thereof from 106 to 135 mm and the midpoint of the next lower lamp being spaced along the wall above said wall midpoint from 36 to 60 mm, the midpoint of said third lowest lamp being spaced downwardly along said wall from said wall midpoint from 36 to 60 mm and the midpoint of the lowermost lamp being spaced downwardly along said wall from said wall midpoint from 106 to 135 mm;

the surfaces of the uppermost lamp and the lowermost lamp being spaced perpendicular to the specimen supporting wall from 45 to 50 mm, the surfaces of the next lower lamp and the third lowest lamp being spaced perpendicular to the specimen supporting wall from 51 to 60 mm.

* * * * *